US012428397B2

(12) United States Patent
Hicks et al.

(10) Patent No.: US 12,428,397 B2
(45) Date of Patent: Sep. 30, 2025

(54) FACTOR XI ACTIVATION INHIBITORS

(71) Applicant: Merck Sharp & Dohme LLC, Rahway, NJ (US)

(72) Inventors: Jacqueline D. Hicks, Watchung, NJ (US); John S. Debenham, Scotch Plains, NJ (US); Amjad Ali, Freehold, NJ (US); Ying-Duo Gao, Middletown, NJ (US); Lan Wei, Berkeley Heights, NJ (US); Dexi Yang, Livingston, NJ (US); Rongze Kuang, Green Brook, NJ (US); Alan Hruza, Hackettstown, NJ (US); Peter Nizner, Fanwood, NJ (US); Daniel A. Tatosian, Berkeley Heights, NJ (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 528 days.

(21) Appl. No.: 17/920,943

(22) PCT Filed: May 7, 2021

(86) PCT No.: PCT/US2021/031208
§ 371 (c)(1),
(2) Date: Oct. 24, 2022

(87) PCT Pub. No.: WO2021/231191
PCT Pub. Date: Nov. 18, 2021

(65) Prior Publication Data
US 2023/0167085 A1 Jun. 1, 2023

Related U.S. Application Data

(60) Provisional application No. 63/023,587, filed on May 12, 2020.

(51) Int. Cl.
*C07D 401/14* (2006.01)
*C07D 417/14* (2006.01)

(52) U.S. Cl.
CPC ......... *C07D 401/14* (2013.01); *C07D 417/14* (2013.01)

(58) Field of Classification Search
CPC ................ C07D 1/14; C07D 417/14
See application file for complete search history.

(56) References Cited

U.S. PATENT DOCUMENTS 9,388,165 B2   7/2016  Bae et al.

FOREIGN PATENT DOCUMENTS

| WO | 2012056372 A1 | 5/2012 |
| WO | 2013056034 A1 | 4/2013 |
| WO | 2016112284 A1 | 7/2016 |
| WO | WO2016112284 | * 7/2016 |
| WO | 2018093695 A1 | 5/2018 |
| WO | 2020243049 A1 | 12/2020 |

OTHER PUBLICATIONS

Al-Horani et al., Factor XIa inhibotrs: A review of the patent literature, Expert Opinion on Therapeutic Patents, vol. 26 No. 3, 323-345, 2016.
Chou, Ting-Chao et al., Quantitative Analysis of Dose-Effect Relationships: The Combined Effects of Multiple Drugs or Enzyme Inhibitors, Adv. Enzyme Regul., 1984, 27-55, 22.
Colman, Robert W., Contact Activation Pathway: Inflammatory, Fibrinolytic, Anticoagulant, Antiadhesive, and Antiangiogenic Activities, Hemostasis and Thrombosis, 2001, 103-121, Chapter 6.
Daiss, Jurgen, O. et al., Sila-venlafaxine, a Sila-Analogue of the Serotonin/Noradrenaline Reuptake Inhibitor Venlafaxine: Synthesis, Crystal Structure Analysis, and Pharmacological Characterization, Organometallics, 2006, pp. 1188-1198, vol. 25.
Kleinschnitz, Christoph et al., Targeting coagulation factor XII provides protection from pathological thrombosis in cerebral ischemia without interfering with hemostasis, JEM, 2006, 513-518, 203.
Renné, Thomas et al., Defective thrombus formation in mice lacking coagulation factor XII, JEM, 2005, 271-281, 202.
Schmaier, Alvin H., Contact Activation, Thrombosis and Hemorrhage, 1998, 105-127, Chapter 5.
Shariat-Madar, Zia et al., Bradykinin B2 receptor knockout mice are protected from thrombosis by increased nitric oxide and prostacyclin, Blood, 2006, 192-199, 108.
Showell, Graham, A. et al., (R)-Sila-venlafaxine: A selective noradrenaline reuptake inhibitor for the treatment of emesis, Bioorganic & Medicinal Chemistry Letters, 2006, pp. 2555-2558, vol. 16.

* cited by examiner

*Primary Examiner* — Brandon J Fetterolf

(74) *Attorney, Agent, or Firm* — Daniel Woods; John C. Todaro

(57) ABSTRACT

The present invention provides a compound of Formula (I) and pharmaceutical compositions comprising one or more said compounds, and methods for using said compounds for treating or preventing thromboses, embolisms, hypercoagulability or fibrotic changes. The compounds are selective Factor XI activation inhibitors.

13 Claims, No Drawings

FACTOR XI ACTIVATION INHIBITORS

CROSS-REFERENCE TO RELATED APPLICATIONS

This application is a National Stage application of International Patent Application No. PCT/US2021/031208, filed May 7, 2021, which claims the benefit of priority to U.S. Provisional Patent Application No. 63/023,587, filed May 12, 2020.

BACKGROUND OF THE INVENTION

Factor XI undergoes proteolysis to afford its activated form, factor XIa, which functions as a plasma serine protease involved in the regulation of blood coagulation. While blood coagulation is a necessary and important part of the regulation of an organism's homeostasis, abnormal blood coagulation can also have deleterious effects. For instance, thrombosis is the formation or presence of a blood clot inside a blood vessel or cavity of the heart. Such a blood clot can lodge in a blood vessel, blocking circulation and inducing a heart attack or stroke. Thromboembolic disorders are the largest cause of mortality and disability in the industrialized world.

Blood clotting is a process of control of the blood stream essential for the survival of mammals. The process of clotting, and the subsequent dissolution of the clot after wound healing has taken place, commence after vascular damage, and can be divided into four phases. The first phase, vasoconstriction or vasocontraction, can cause a decrease in blood loss in the damaged area. In the next phase, platelet activation by thrombin, platelets attach to the site of the vessel wall damage and form a platelet aggregate. In the third phase, formation of clotting complexes leads to massive formation of thrombin, which converts soluble fibrinogen to fibrin by cleavage of two small peptides. In the fourth phase, after wound healing, the thrombus is dissolved by the action of the key enzyme of the endogenous fibrinolysis system, plasmin.

Two alternative pathways can lead to the formation of a fibrin clot, the intrinsic and the extrinsic pathway. These pathways are initiated by different mechanisms, but in the later phase they converge to give a common final path of the clotting cascade. In this final path of clotting, clotting factor X is activated. The activated factor X is responsible for the formation of thrombin from the inactive precursor prothrombin circulating in the blood. The formation of a thrombus on the bottom of a vessel wall abnormality without a wound is the result of the intrinsic pathway. Fibrin clot formation as a response to tissue damage or an injury is the result of the extrinsic pathway. Both pathways comprise a relatively large number of proteins, which are known as clotting factors. The intrinsic pathway requires the clotting factors V, VIII, IX, X, XI and XII and also prekallikrein, high molecular weight kininogen, calcium ions and phospholipids from platelets. The activation of factor XI to generate factor XIa is a central point of intersection between the two pathways of activation of clotting. Factor XIa has an important role in blood clotting.

Coagulation is initiated when blood is exposed to artificial surfaces (e.g., during hemodialysis, "on-pump" cardiovascular surgery, vessel grafts, bacterial sepsis), on cell surfaces, cellular receptors, cell debris, DNA, RNA, and extracellular matrices. This process is also termed contact activation. Surface absorption of factor XII leads to a conformational change in the factor XII molecule, thereby facilitating activation to proteolytic active factor XII molecules (factor XIIa and factor XIIf). Factor XIIa (or XIIf) has a number of target proteins, including plasma prekallikrein and factor XI. Active plasma kallikrein further activates factor XII, leading to an amplification of contact activation. Alternatively, the serine protease prolylcarboxylpeptidase can activate plasma kallikrein complexed with high molecular weight kininogen in a multiprotein complex formed on the surface of cells and matrices (Shariat-Madar et al., Blood, 108:192-199 (2006)). Contact activation is a surface mediated process responsible in part for the regulation of thrombosis and inflammation, and is mediated, at least in part, by fibrinolytic-, complement-, kininogen/kinin-, and other humoral and cellular pathways (for review, Coleman, R., "Contact ActivationPathway", Hemostasis and Thrombosis, pp. 103-122, Lippincott Williams & Wilkins (2001); Schmaier, A. H., "Contact Activation", Thrombosis and Hemorrhage, pp. 105-128 (1998)). The biological relevance of the contact activation system for thromboembolic diseases is supported by the phenotype of factor XII deficient mice. More specifically, factor XII deficient mice were protected from thrombotic vascular occlusion in several thrombosis models as well as stroke models and the phenotype of the XII deficient mice was identical to XI deficient mice (Renne et al., J Exp. Med., 202:271-281 (2005); Kleinschmitz et al., J Exp. Med., 203:513-518 (2006)). The fact that factor XI is downstream from factor XIIa, combined with the identical phenotype of the XII and XI deficient mice suggest that the contact activation system could play a major role in factor XI activation in vivo.

SUMMARY OF THE INVENTION

The present invention relates to compounds of Formula I:

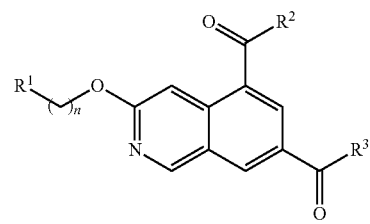

and pharmaceutically acceptable salts thereof. The compounds of Formula I are selective Factor XI activation inhibitors, and as such may be useful in the treatment, inhibition or amelioration of one or more disease states that could benefit from inhibition of Factor XI, including thromboses, embolisms, hypercoagulability or fibrotic changes. The compounds of this invention could further be used in combination with other therapeutically effective agents, including but not limited to, other drugs useful for the treatment of thromboses, embolisms, hypercoagulability or fibrotic changes. The invention furthermore relates to processes for preparing compounds of Formula I, and pharmaceutical compositions which comprise compounds of Formula I and pharmaceutically acceptable salts thereof.

DETAILED DESCRIPTION OF THE INVENTION

The present invention relates to compounds of Formula I:

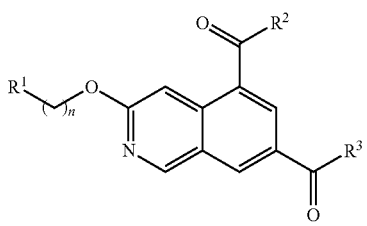

wherein $R^1$ is phenyl or heteroaryl, which may be monocyclic or bicyclic, wherein said phenyl and heteroaryl groups are optionally substituted with one to three substituents independently selected from the group consisting of halo, oxo, cyano, $R^4$ and $OR^4$;

$R^2$ is piperidinyl or $NR^4R^5$, wherein said piperidinyl group is optionally substituted with one to three halo;

$R^3$ is heterocyclyl, which is optionally substituted with one to three substituents independently selected from the group consisting of halo, cyano, $R^4$, $OR^4$ and $R^6$;

$R^4$ is hydrogen or $C_{1-6}$ alkyl, which is optionally substituted with one to three halo;

$R^5$ is hydrogen or $C_{1-6}$ alkyl, which is optionally substituted with one to three halo;

$R^6$ is phenyl, $C_{3-6}$ cycloalkyl, heterocyclyl or heteroaryl, wherein said heteroaryl is optionally substituted with one to three substituents independently selected from the group consisting of $C_{1-6}$ alkyl and halo;

n is an integer from one to three;

or a pharmaceutically acceptable salt thereof.

In an embodiment of the invention, $R^1$ is benzothiazolyl, phenyl or pyridinyl wherein said groups are optionally substituted with one or two substituents independently selected from the group consisting of chloro, cyano and $CF_3$. In a class of the invention, $R^1$ is pyridinyl, which is optionally substituted with one or two substituents independently selected from the group consisting of chloro, cyano and $CF_3$. In another class of the invention, $R^1$ is benzothiazolyl. In another class of the invention, $R^1$ is phenyl, which is optionally substituted with one or two substituents independently selected from the group consisting of chloro and cyano.

In an embodiment of the invention, $R^2$ is piperidinyl.

In an embodiment of the invention, $R^3$ is piperidinyl, which is optionally substituted with one or two substituents independently selected from the group consisting of cyano, pyrazolyl, methylpyrazolyl, phenyl and triazolyl. In a class of the invention, $R^3$ is piperidinyl, which is optionally substituted with cyano and phenyl.

In an embodiment of the invention, n is one. In another embodiment of the invention, n is two. In another embodiment of the invention, n is three.

Reference to the preferred classes and subclasses set forth above is meant to include all combinations of particular and preferred groups unless stated otherwise.

Specific embodiments of the present invention include, but are not limited to the compounds identified herein as Examples 1 to 16, or pharmaceutically acceptable salts thereof.

Also included within the scope of the present invention is a pharmaceutical composition which is comprised of a compound of Formula I as described above and a pharmaceutically acceptable carrier. The invention is also contemplated to encompass a pharmaceutical composition which is comprised of a pharmaceutically acceptable carrier and any of the compounds specifically disclosed in the present application. These and other aspects of the invention will be apparent from the teachings contained herein.

The invention also includes compositions for inhibiting loss of blood platelets, inhibiting formation of blood platelet aggregates, inhibiting formation of fibrin, inhibiting thrombus formation, inhibiting embolus formation, treating inflammatory disorders, treating diabetic retinopathy and treating hereditary angioedema in a mammal, comprising a compound of the invention in a pharmaceutically acceptable carrier. These compositions may optionally include anticoagulants, antiplatelet agents, and thrombolytic agents. The compositions can be added to blood, blood products, or mammalian organs in order to effect the desired inhibitions.

The invention also includes compositions for preventing or treating unstable angina, refractory angina, myocardial infarction, transient ischemic attacks, atrial fibrillation, thrombotic stroke, embolic stroke, deep vein thrombosis, disseminated intravascular coagulation, ocular buildup of fibrin, and reocclusion or restenosis of recanalized vessels, in a mammal, comprising a compound of the invention in a pharmaceutically acceptable carrier. These compositions may optionally include anticoagulants, antiplatelet agents, and thrombolytic agents.

The invention also includes methods for treating unstable angina, refractory angina, myocardial infarction, transient ischemic attacks, atrial fibrillation, thrombotic stroke, embolic stroke, deep vein thrombosis, disseminated intravascular coagulation, ocular buildup of fibrin, and reocclusion or restenosis of recanalized vessels, comprising administering a composition of the compound of the invention to a mammal in need thereof.

The invention also includes a method for reducing the thrombogenicity of a surface in a mammal by attaching to the surface, either covalently or noncovalently, a compound of the invention.

The invention also includes a compound of the invention, or a pharmaceutically acceptable salt thereof, for use in the manufacture of a medicament for inhibiting thrombin, inhibiting thrombus formation, treating thrombus formation or preventing thrombus formation in a mammal. In addition, the invention includes a compound of the invention, or a pharmaceutically acceptable salt thereof, for use in therapy.

Compounds of the invention are Factor XI activation inhibitors and may have therapeutic value in, for example, preventing coronary artery disease. The compounds of the invention have improved pharmacokinetic profiles compared to compounds known in the art. Furthermore, some of the compounds of the invention have a better combination of potency, efficacy and pharmacokinetic properties compared to known compounds.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, adipate, alginate, aspirate, benzenesulfonate, benzoate, bicarbonate, bisulfate, bitartrate, borate, bromide, butyrate, camphorate, camphorsulfonate, camsylate, carbonate, chloride, clavulanate, citrate, cyclopentane propionate, diethylacetic, digluconate, dihydrochloride, dodecylsulfanate, edetate, edisylate, estolate, esylate, ethanesulfonate, formic, fumarate, gluceptate, glucoheptanoate, gluconate, glutamate, glycerophosphate, glycollylarsanilate, hemisulfate, heptanoate, hexanoate, hexylresorcinate, hydrabamine, hydrobromide, hydrochloride, 2-hydroxyethanesulfonate, hydroxynaphthoate, iodide, isonicotinic, isothionate, lactate, lactobionate, laurate, malate, maleate, mandelate, mesylate, methylbromide, methylnitrate, methylsulfate, methanesulfonate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, phosphate/diphosphate, pimelic, phenylpropionic, polygalacturonate, propionate, salicylate, stearate, sulfate, subacetate, succinate, tannate, tartrate, teoclate, thiocyanate, tosylate, triethiodide, trifluoroacetate, undeconate, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Also included are the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Also, included are the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

These salts can be obtained by known methods, for example, by mixing a compound of the present invention with an equivalent amount and a solution containing a desired acid, base, or the like, and then collecting the desired salt by filtering the salt or distilling off the solvent. The compounds of the present invention and salts thereof may form solvates with a solvent such as water, ethanol, or glycerol. The compounds of the present invention may form an acid addition salt and a salt with a base at the same time according to the type of substituent of the side chain.

If the compounds of Formula I simultaneously contain acidic and basic groups in the molecule the invention also includes, in addition to the salt forms mentioned, inner salts or betaines (zwitterions).

The present invention encompasses all stereoisomeric forms of the compounds of Formula I. Unless a specific stereochemistry is indicated, the present invention is meant to comprehend all such isomeric forms of these compounds.

Centers of asymmetry that are present in the compounds of Formula I can all independently of one another have (R) configuration or (S) configuration. When bonds to the chiral carbon are depicted as straight lines in the structural Formulas of the invention, it is understood that both the (R) and (S) configurations of the chiral carbon, and hence both each individual enantiomer and mixtures thereof, are embraced within the Formula. When a particular configuration is depicted, that entantiomer (either (R) or (S), at that center) is intended. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

Unless a specific enantiomer or diastereomer is indicated, the invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the transform as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. The present invention includes all such isomers, as well as salts, solvates (including hydrates) and solvated salts of such racemates, enantiomers, diastereomers and tautomers and mixtures thereof.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the specifically and generically described compounds. For example, different isotopic forms of hydrogen (H) include protium ($1_H$) and deuterium ($2_H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques well known to those skilled in the art or by processes analogous to those described in the general process schemes and examples herein using appropriate isotopically-enriched reagents and/or intermediates.

When any variable occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off-target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted" (with one or more substituents) should be understood as meaning that the group in question is either unsubstituted or may be substituted with one or more substituents.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with unsolvated and anhydrous forms.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO— depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$alkyl esters and —$C_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc.

As used herein, and throughout this disclosure, the following terms, unless otherwise indicated, shall be understood to have the following meanings:

A "subject" is a human or non-human mammal. In one embodiment, a subject is a human. In another embodiment, a subject is a primate. In another embodiment, a subject is a monkey. In another embodiment, a subject is a chimpanzee. In still another embodiment, a subject is a rhesus monkey.

As used herein, the terms "treatment" and "treating" refer to all processes in which there may be a slowing, interrupting, arresting, controlling, or stopping of the progression of a disease or disorder described herein. The terms do not necessarily indicate a total elimination of all disease or disorder symptoms.

The terms "preventing," or "prophylaxis," as used herein, refers to reducing the likelihood of contracting disease or disorder described herein, or reducing the severity of a disease or disorder described herein.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 4 carbon atoms ($C_1$-$C_4$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. In one embodiment, an alkyl group is linear. In another embodiment, an alkyl group is branched. Unless otherwise indicated, an alkyl group is unsubstituted.

The term "halo," as used herein, means —F, —Cl, —Br or —I.

The term "cycloalkyl" means a monocyclic or bicyclic saturated aliphatic hydrocarbon group having the specified number of carbon atoms. For example, "cycloalkyl" includes cyclopropyl, cyclobutyl, cyclopentyl, cyclohexyl, and so on. Bicyclic cycloalkyl ring systems include fused ring systems, where two rings share two atoms, and spiro ring systems, where two rings share one atom.

The term "heteroaryl", as used herein, represents a stable monocyclic or bicyclic ring system of up to 10 atoms in each ring, wherein at least one ring is aromatic, and at least one ring contains from 1 to 4 heteroatoms selected from the group consisting of O, N and S. Bicyclic heteroaryl ring systems include fused ring systems, where two rings share two atoms, and spiro ring systems, where two rings share one atom. Heteroaryl groups within the scope of this definition include but are not limited to: azaindolyl, benzoimidazolyl, benzisoxazolyl, benzofuranyl, benzofurazanyl, benzopyrazolyl, benzotriazolyl, benzothiophenyl, benzoxazolyl, carbazolyl, carbolinyl, cinnolinyl, dihydroindenyl, furanyl, indolinyl, indolyl, indolazinyl, indazolyl, isobenzofuranyl, isoindolyl, isoquinolyl, isothiazolyl, isoxazolyl, naphthalenyl, naphthpyridinyl, oxadiazolyl, oxazolyl, oxazoline, isoxazoline, pyranyl, pyrazinyl, pyrazolyl, pyrazolopyrimidinyl, pyridazinyl, pyridopyridinyl, pyridyl, pyrimidinyl, pyrrolyl, quinazolinyl, quinolyl, quinoxalinyl, tetrazolyl, tetrazolopyridyl, thiadiazolyl, thiazolyl, thienyl, triazolyl, dihydrobenzoimidazolyl, dihydrobenzofuranyl, dihydrobenzothiophenyl, dihydrobenzoxazolyl, dihydroindolyl, dihydroquinolinyl, dihydrobenzodioxinyl, dihydropyrazoloxazinyl, dihydropyrazolyothiazinedioxidyl, methylenedioxybenzene, benzothiazolyl, benzothienyl, quinolinyl, isoquinolinyl, oxazolyl, tetra-hydroquinoline and 3-oxo-3,4dihydro-2N-benzo[b][1,4]thiazine. If the heteroaryl contains nitrogen atoms, it is understood that the corresponding N-oxides thereof are also encompassed by this definition.

The term "heterocycle" or "heterocyclyl" as used herein is intended to mean a stable nonaromatic monocyclic or bicyclic ring system of up to 10 atoms in each ring, unless otherwise specified, containing from 1 to 4 heteroatoms selected from the group consisting of O, N, S, SO, or $SO_2$. Bicyclic heterocyclic ring systems include fused ring systems, where two rings share two atoms, and spiro ring systems, where two rings share one atom. "Heterocyclyl" therefore includes, but is not limited to the following: azaspirononanyl, azaspirooctanyl, azetidinyl, dioxanyl, oxadiazaspirodecenyl, oxaspirooctanyl, oxazolidinonyl, piperazinyl, piperidinyl, pyrrolidinyl, morpholinyl, thiomorpholinyl, tetrahydrofurnayl, tetrahydropyranyl, dihydropiperidinyl, tetrahydrothiophenyl and the like. If the heterocycle contains a nitrogen, it is understood that the corresponding N-oxides thereof are also encompassed by this definition.

"Celite®" (Fluka) diatomite is diatomaceous earth, and can be referred to as "celite".

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any substituent or variable (e.g., $R^4$) occurs more than one time in any constituent or in Formula I, its definition on each occurrence is independent of its definition at every other occurrence, unless otherwise indicated.

As used herein, the term "composition" is intended to encompass a product comprising the specified ingredients in the specified amounts, as well as any product which results from combination of the specified ingredients in the specified amounts.

The invention also relates to medicaments containing at least one compound of the Formula I and/or of a pharmaceutically acceptable salt of the compound of the Formula I and/or an optionally stereoisomeric form of the compound of the Formula I or a pharmaceutically acceptable salt of the stereoisomeric form of the compound of Formula I, together with a pharmaceutically suitable and pharmaceutically acceptable vehicle, additive and/or other active substances and auxiliaries.

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, humans, sheep, horses, cattle, pigs, dogs, cats, rats, and mice.

Inhibition of the generation of Factor XIa is a useful mean of anticoagulant therapy that can be achieved by inhibition of the activation of zymogen Factor XI. Factor XI activation inhibitors are useful anticoagulants not only in individuals having thrombotic conditions but are useful whenever inhibition of blood coagulation is required such as to prevent coagulation of stored whole blood and to prevent coagulation in other biological samples for testing or storage. Thus, the Factor XI activation inhibitors can be added to or contacted with any medium containing or suspected of containing thrombin and in which it is desired that blood coagulation be inhibited, e.g., when contacting the mammal's blood with material selected from the group consisting of vascular grafts, stents, orthopedic prosthesis, cardiac prosthesis, and extracorporeal circulation systems.

Compounds of the invention may be useful for treating or preventing venous thromboembolism (e.g., obstruction or occlusion of a vein by a detached thrombus; obstruction or occlusion of a lung artery by a detached thrombus), cardiogenic thromboembolism (e.g., obstruction or occlusion of the heart by a detached thrombus), arterial thrombosis (e.g., formation of a thrombus within an artery that may cause infarction of tissue supplied by the artery), atherosclerosis (e.g., arteriosclerosis characterized by irregularly distributed lipid deposits) in mammals, and for lowering the propensity of devices that come into contact with blood to clot blood.

Examples of venous thromboembolism which may be treated or prevented with compounds of the invention include obstruction of a vein, obstruction of a lung artery (pulmonary embolism), deep vein thrombosis, thrombosis associated with cancer and cancer chemotherapy, thrombosis inherited with thrombophilic diseases such as Protein C deficiency, Protein S deficiency, antithrombin III deficiency, and Factor V Leiden, and thrombosis resulting from acquired thrombophilic disorders such as systemic lupus erythematosus (inflammatory connective tissue disease). Also, with regard to venous thromboembolism, compounds of the invention may be useful for maintaining patency of indwelling catheters.

Examples of cardiogenic thromboembolism which may be treated or prevented with compounds of the invention include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples of arterial thrombosis include unstable angina (severe constrictive pain in chest of coronary origin), myocardial infarction (heart muscle cell death resulting from insufficient blood supply), ischemic heart disease (local anemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also, with regard to arterial thrombosis, compounds of the invention may be useful for maintaining patency in arteriovenous cannulas.

Examples of atherosclerosis include arteriosclerosis.

Examples of devices that come into contact with blood include vascular grafts, stents, orthopedic prosthesis, cardiac prosthesis, and extracorporeal circulation systems.

The medicaments according to the invention can be administered by oral, inhalative, rectal or transdermal administration or by subcutaneous, intraarticular, intraperitoneal or intravenous injection. Oral administration is preferred. Coating of stents with compounds of the Formula (I) and other surfaces which come into contact with blood in the body is possible.

The invention also relates to a process for the production of a medicament, which comprises bringing at least one compound of the Formula (I) into a suitable administration form using a pharmaceutically suitable and pharmaceutically acceptable carrier and optionally further suitable active substances, additives or auxiliaries.

Suitable solid or galenical preparation forms are, for example, granules, powders, coated tablets, tablets, (micro) capsules, suppositories, syrups, juices, suspensions, emulsions, drops or injectable solutions and preparations having prolonged release of active substance, in whose preparation customary excipients such as vehicles, disintegrants, binders, coating agents, swelling agents, glidants or lubricants, flavorings, sweeteners and solubilizers are used. Frequently used auxiliaries which may be mentioned are magnesium carbonate, titanium dioxide, lactose, mannitol and other sugars, talc, lactose, gelatin, starch, cellulose and its derivatives, animal and plant oils such as cod liver oil, sunflower, peanut or sesame oil, polyethylene glycol and solvents such as, for example, sterile water and mono- or polyhydric alcohols such as glycerol.

The dosage regimen utilizing the Factor XI activation inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the Factor XI activation inhibitors, when used for the indicated effects, will range between about 0.01 mg per kg of body weight per day (mg/kg/day) to about 30 mg/kg/day, preferably 0.025-7.5 mg/kg/day, more preferably 0.1-2.5 mg/kg/day, and most preferably 0.1-0.5 mg/kg/day (unless specified otherwise, amounts of active ingredients are on free base basis). For example, an 80 kg patient would receive between about 0.8 mg/day and 2.4 g/day, preferably 2-600 mg/day, more preferably 8-200 mg/day, and most preferably 8-40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the Factor XI activation inhibitors may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025-7.5 mg/kg/day, preferably 0.1-2.5 mg/kg/day, and more preferably 0.1-0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01-1.0 mg/mL, e.g. 0.1 mg/mL, 0.3 mg/mL, and 0.6 mg/mL, and administered in amounts per day of between 0.01 mL/kg patient weight and 10.0 mL/kg patient weight, e.g. 0.1 mL/kg, 0.2 mL/kg, 0.5 mL/kg. In one example, an 80 kg patient, receiving 8 mL twice a day of an intravenous formulation having a concentration of active ingredient of 0.5 mg/mL, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. The choice of appropriate buffer and pH of a formulation, depending on solubility of the drug to be administered, is readily made by a person having ordinary skill in the art.

Compounds of Formula I can be administered both as a monotherapy and in combination with other therapeutic agents, including antithrombotics (anticoagulants and platelet aggregation inhibitors), thrombolytics (plasminogen activators), other profibrinolytically active substances, hypotensives, blood sugar regulators, lipid-lowering agents and antiarrhythmics.

The Factor XI activation inhibitors can also be co-administered with suitable anticoagulants, including, but not limited to, factor XIa inhibitors, thrombin inhibitors, thrombin receptor antagonists, factor VIIa inhibitors, factor Xa inhibitors, factor IXa inhibitors, factor XIIa inhibitors, adenosine diphosphate antiplatelet agents (e.g., P2Y12 antagonists), fibrinogen receptor antagonists (e.g. to treat or prevent unstable angina or to prevent reocclusion after angioplasty and restenosis), other anticoagulants such as aspirin, and thrombolytic agents such as plasminogen activators or streptokinase to achieve synergistic effects in the treatment of various vascular pathologies. Such anticoagulants include, for example, apixaban, dabigatran, cangrelor, ticagrelor, vorapaxar, clopidogrel, edoxaban, mipomersen, prasugrel, rivaroxaban, and semuloparin. For example, patients suffering from coronary artery disease, and patients subjected to angioplasty procedures, would benefit from coadministration of fibrinogen receptor antagonists and thrombin inhibitors. Factor XI Activation Inhibitors may be administered first following thrombus formation, and tissue plasminogen activator or other plasminogen activator is administered thereafter.

Alternatively or additionally, one or more additional pharmacologically active agents may be administered in combination with a compound of the invention. The additional active agent (or agents) is intended to mean a pharmaceutically active agent (or agents) that is active in the body, including pro-drugs that convert to pharmaceutically active form after administration, which is different from the compound of the invention, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of the invention in a single dosage formulation (a fixed dose drug combination), or may be administered to the patient in one or more separate dosage formulations which allows for concurrent or sequential administration of the active agents (co-administration of the separate active agents). Examples of additional active agents which may be employed include but are not limited to angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); angiotensin II receptor antagonists also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TEVETAN®), irbesartan (AVAPRO®), losartan, e.g., losartan potassium (COZAAR®), olmesartan, e.g, olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®, etc.); potassium sparing diuretics such as amiloride HCl, spironolactone, eplerenone, triamterene, each with or without HCTZ; neutral endopeptidase inhibitors (e.g., thiorphan and phosphoramidon); aldosterone antagonists; aldosterone synthase inhibitors; renin inhibitors; enalkrein; RO 42-5892; A 65317; CP 80794; ES 1005; ES 8891; SQ 34017; aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine); potassium channel activators (e.g., nicorandil, pinacidil, cromakalim, minoxidil, aprilkalim, loprazolam); sympatholytics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazosin, prazosin or alpha methyldopa); central alpha adrenergic agonists; peripheral vasodilators (e.g. hydralazine); lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; inhibitors of glucose uptake, such as sodium-glucose transporter (SGLT) inhibitors and its various isoforms, such as SGLT-1, SGLT-2 (e.g., ASP-1941, TS-071, BI-10773, tofogliflozin, LX-4211, canagliflozin, dapagliflozin, ertugliflozin, ipragliflozin and remogliflozin), and SGLT-3; or with other drugs beneficial for the prevention or the treatment of the above-mentioned diseases including but not limited to diazoxide; and including the free-acid, free-base, and pharmaceutically acceptable salt forms, pro-drug forms, e.g., esters, and salts of pro-drugs of the above medicinal agents, where chemically possible. Trademark names of pharmaceutical drugs noted above are provided for exemplification of the marketed form of the active agent(s); such pharmaceutical drugs could be used in a separate dosage form for concurrent or sequential administration with a compound of the invention, or the active agent(s) therein could be used in a fixed dose drug combination including a compound of the invention.

Typical doses of Factor XI activation inhibitors of the invention in combination with other suitable anti-platelet agents, anticoagulation agents, or thrombolytic agents may be the same as those doses of Factor XI activation inhibitors administered without coadministration of additional anti-platelet agents, anticoagulation agents, or thrombolytic agents, or may be substantially less that those doses of thrombin inhibitors administered without coadministration of additional anti-platelet agents, anticoagulation agents, or thrombolytic agents, depending on a patient's therapeutic needs.

The compounds are administered to a mammal in a therapeutically effective amount. By "therapeutically effective amount" it is meant an amount of a compound of the present invention that, when administered alone or in combination with an additional therapeutic agent to a mammal, is effective to treat (i.e., prevent, inhibit or ameliorate) the thromboembolic and/or inflammatory disease condition or treat the progression of the disease in a host.

The compounds of the invention are preferably administered alone to a mammal in a therapeutically effective amount. However, the compounds of the invention can also be administered in combination with an additional therapeutic agent, as defined below, to a mammal in a therapeutically effective amount. When administered in a combination, the combination of compounds is preferably, but not necessarily, a synergistic combination. Synergy, as described for example by Chou and Talalay, *Adv. Enzyme Regul.* 1984, 22, 27-55, occurs when the effect (in this case, inhibition of the desired target) of the compounds when administered in combination is greater than the additive effect of each of the compounds when administered individually as a single agent. In general, a synergistic effect is most clearly demonstrated at suboptimal concentrations of the compounds. Synergy can be in terms of lower cytotoxicity, increased anticoagulant effect, or some other beneficial effect of the combination compared with the individual components.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

The present invention is not limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claims.

General Methods

Several methods for preparing the compounds of this invention are illustrated in the following Schemes and Examples. Starting materials and the requisite intermediates are in some cases commercially available, or can be prepared according to literature procedures or as illustrated herein. The compounds of this invention may be prepared by employing reactions as shown in the following schemes, in addition to other standard manipulations that are known in the literature or exemplified in the experimental procedures. Substituent numbering as shown in the schemes does not necessarily correlate to that used in the claims and often, for clarity, a single substituent is shown attached to the compound where multiple substituents are allowed under the definitions hereinabove. Reactions used to generate the compounds of this invention are carried out by employing reactions as shown in the schemes and examples herein, in addition to other standard manipulations such as ester hydrolysis, cleavage of protecting groups, etc., as may be known in the literature or exemplified in the experimental procedures. Starting materials are made according to procedures known in the art or as illustrated herein.

The compounds of the present invention can be prepared in a variety of fashions. In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. Because the schemes are an illustration, the invention should not be construed as being limited by the chemical reactions and conditions expressed. The preparation of the various starting materials used herein is well within the skill of a person versed in the art. The following examples are provided so that the invention might be more fully understood. These examples are illustrative only and should not be construed as limiting the invention in any way. Absolute stereochemistry of separate stereoisomers in the examples and intermediates are not determined unless stated otherwise in an example or explicitly in the nomenclature.

NMR spectra were measured on VARIAN or Bruker NMR Systems (400, 500 or 600 MHz). Chemical shifts are reported in ppm downfield and up field from tetramethylsilane (TMS) and referenced to either internal TMS or solvent resonances ($^1$H NMR: δ 7.27 for CDCl$_3$, δ 2.50 for (CD$_3$)(CHD$_2$)SO, and $^{131}$C NMR: δ 77.02 for CDCl$_3$, δ 39.51 for (CD$_3$)$_2$SO. Coupling constants (J) are expressed in hertz (Hz), and spin multiplicities are given as s (singlet), d (doublet), dd (double doublet), t (triplet), m (multiplet), and br (broad). Chiral resolutions were performed on either Waters Thar 80 SFC or Berger MG II preparative SFC systems. LC-MS data were recorded on SHIMADAZU LC-MS-2020, SHIMADAZU LC-MS-2010EV, or Agilent 1100 series LC-MS, Agilent Prime-1260, or Waters Acquity LC-MS instruments using C18 columns employing a MeCN gradient in water containing 0.02 to 0.1% TFA. UV detections were at 220 and/or 254 nm and ESI ionization was used for MS detection.

When chiral resolution was achieved by chromatography using chiral columns, the chiral columns used for SFC chiral resolutions are listed in tables. Some of the chiral columns used were CHIRALPAK AD, CHIRALCEL OJ, CHIRALPAK AS, CHIRALPAK AY, CHIRALPAK IA, CHIRALPAK AD-H, and CHIRALPAK AS-H. Henceforth, they will be referred by their two or three letter abbreviations. As a convention, the fast-eluting isomer from a chiral resolution is always listed first in this table followed immediately by the slower-eluting isomer from the same resolution. If more than two isomers were separated, they will be always listed in the tables in order they were eluted, such as Peak 1 followed by Peak 2, Peak 3 and so on.

Also, TLC is thin layer chromatography; UV is ultraviolet; W is watts; wt. % is percentage by weight; xg is times gravity; α$_D$ is the specific rotation of polarized light at 589 nm; ° C. is degrees Celsius; % w/v is percentage in weight of the former agent relative to the volume of the latter agent; Hz is hertz; cpm is counts per minute; δ$_H$ is chemical shift; d is doublet; dd is doublet of doublets; MHz is megahertz; MS is mass spectrum, and a mass spectrum obtained by ES-MS may be denoted herein by "LC-MS"; m/z is mass to charge ratio; n is normal; N is normal; nm is nanometer; nM is nanomolar.

Several catalysts and ligands are used in the following procedures. "XANTPHOS" is also known as 4,5-bis(diphenylphosphino)-9,9-dimethylxanthene and "Dppf" is also known as 1,1'-bis(diphenylphosphino)ferrocene. "Xantphos Pd G3" is also know as [(4,5-Bis(diphenylphosphino)-9,9-dimethylxanthene)-2-(2'-amino-1,1'-biphenyl)]palladium (II) methanesulfonate. These ligands and catalyst are available from Millipore Sigma.

For purposes of this specification, the following abbreviations have the indicated meanings:

Ac acetyl
ACN acetonitrile
AcOH or HOAc acetic acid
aq aqueous
Bn benzyl
Boc or BOC tert-butoxycarbonyl
Bu butyl
Bz benzoyl
cBu cyclobutyl
Cbz benyzloxycarbonyl
cPr cyclopropyl
d double
DAST (diethylamino)sulfur trifluoride
dba dibenzylideneacetone
DCE 1,2-dichloroethane
DCM dichloromethane
DIBAL or Dibal-H diisobutylaluminum hydride
DIEA, DIPEA, or Hünig's base N,N-diisopropylethylamine
DMA 1,2-dimethylacetamide
DMAP 4-dimethylaminopyridine
DMF dimethylformamide
DMP Dess-Martin periodinane (1,1,1-triacetoxy)-1,1-dihydro-1,2-benziodoxol-3(1H)-one
DMSO dimethyl sulfoxide
dppf 1,1'-bis(diphenylphosphino)ferrocene
EDC 1-ethyl-3-(3-dimethylaminopropyl)carbodiimide
ESI electrospray ionization
Et ethyl
EtOH ethanol
EA or EtOAc ethyl acetate
g grams
h hour
HATU N,N,N',N'-tetramethyl-O-(7-azabenzotriazol-1-yl)uronium hexafluorophosphate
HMDS 1,1,1,3,3,3-hexamethyldisilazane
HOBt 1-hydroxybenzotriazole
HPLC high-performance liquid chromatography
Hz Hertz
IPA isopropanol
iPr isopropyl
LCMS liquid chromatography mass spectrometry
L liter
LDA lithium diisopropylamide
LHMDS, LiHMDS lithium bis(trimethylsilyl)amide
mCPBA m-choroperoxybenzoic acid
m/z mass-to-charge ratio
Me methyl
MeOH methanol
mg milligrams
MHz megahertz
min minute
μL microliters
mL milliliters
mmol millimoles
MS mass spectrometry
Ms methanesulfonyl (mesyl)
MTBE methyl tert-butyl ether
M Molar
NBS N-bromosuccinimide
NMR nuclear magnetic resonance spectroscopy
Ph phenyl
PMB p-methoxybenzyl
Pr propyl
psi pounds per square inch
rac racemic mixture
RT or rt room temperature (ambient, about 25° C.)
SEM 2-(trimethylsilyl)ethoxy)methyl
SEM-Cl (2-(chloromethoxy)ethyl)trimethylsilane
SFC supercritical fluid chromatography
TBAF tert-butyl ammonium fluoride
TBS or TBDMS tert-butyldimethyl silyl
TBSCl tert-butyldimethylsilyl chloride
TBDPS tert-butyldiphenylsilyl
TBDPSCl tert-butyldiphenylsilyl chloride
tBu tert-butyl
tBu X-phos 2-di-tert-butylphosphino-2',4',6'-triisopropylbiphenyl
TEA triethylamine (Et$_3$N)
Tf Triflate
TFA trifluoroacetic acid
TFAA trifluoroacetic anhydride
THF THF
TLC thin layer chromatography
TMS trimethylsilyl
Trifluoromethylator (1,10-Phenanthroline)(trifluoromethyl)copper(I)
Tris tris(hydroxymethyl)aminomethane
Ts toluenesulfonyl (tolyl)
TSA p-toluenesulfonic acid
X-phos 2-dicyclohexylphosphino-2',4',6'-triisopropylbiphenyl
Xantphos 4,5-bis(diphenylphosphino)-9,9-dimethylxanthene
Xantphos Pd G3 [(4,5-Bis(diphenylphosphino)-9,9-dimethylxanthene)-2-(2'-amino-1,1'-biphenyl)]palladium (II) methanesulfonate General Scheme

SCHEME 1

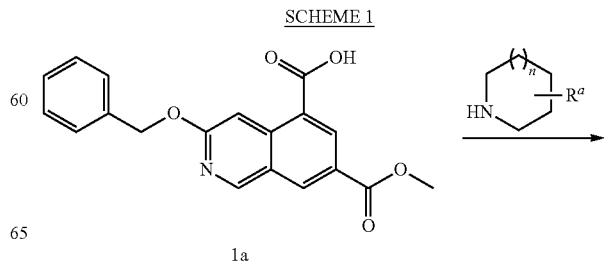

1a

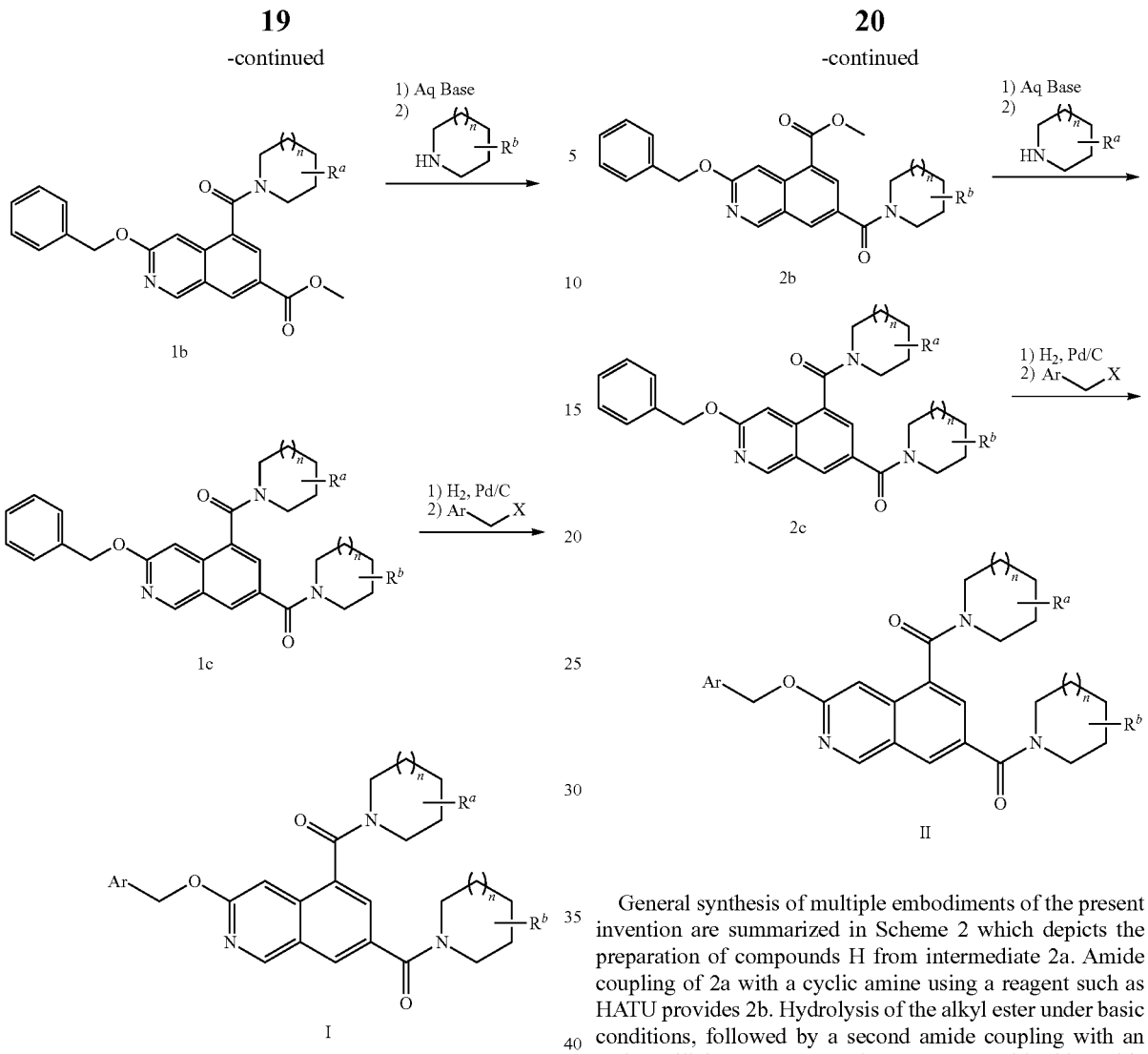

General synthesis of multiple embodiments of the present invention are summarized in Scheme 1 which depicts the preparation of compounds I from intermediate 1a. Amide coupling of 1a with an amine using a reagent such as N,N,N',N'-tetramethyl-O-(7-azabenzotriazol-1-yl)uronium hexafluorophosphate (HATU) provides 1b. Base mediated hydrolysis of the methyl ester, followed by a second amide coupling with an amine utilizing a reagent such as HATU provides bis-amide 1c. Removal of the protecting group, such as a benzyl, with a catalyst such as Pd/C provides the free alcohol. Alkylation of the free alcohol with a benzylic halide or activated benzylic hydroxyl to provides I.

General synthesis of multiple embodiments of the present invention are summarized in Scheme 2 which depicts the preparation of compounds II from intermediate 2a. Amide coupling of 2a with a cyclic amine using a reagent such as HATU provides 2b. Hydrolysis of the alkyl ester under basic conditions, followed by a second amide coupling with an amine utilizing a reagent such as HATU provides bis-amide 2c. Removal of the benzyl protecting group, with a catalyst such as Pd/C under a hydrogen atmosphere provides the free alcohol. Alkylation of the free alcohol with a benzylic halide or activated benzylic hydroxyl to provides II.

INTERMEDIATES

Intermediate 1 and 2

3-(benzyloxy)-7-(methoxycarbonyl)isoquinoline-5-carboxylic acid and 3-(benzyloxy)-5-(methoxycarbonyl)isoquinoline-7-carboxylic acid

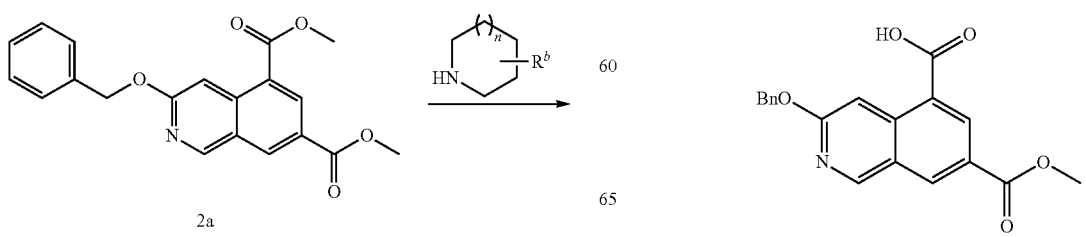

-continued

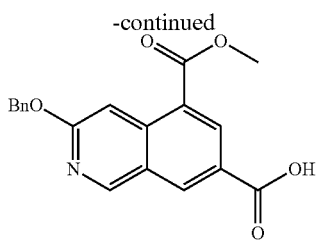

Step A. (3,5-dibromophenyl)methanamine

To a 20-L 4-necked round-bottom flask purged and maintained with an inert atmosphere of nitrogen, was placed a solution of 3,5-dibromobenzonitrile (1000 g, 1 equiv) in THF (5 L). This was followed by the addition of $BH_3 \cdot THF$ (7.66 L, 2.0 equiv, 1 M) dropwise with stirring. The resulting solution was stirred for 2 h at rt. The reaction mixture was cooled to 0° C. with a water/ice bath. The pH value of the solution was adjusted to 2 with HCl (6 mol/L). The resulting solution was stirred for 2 hr at 70° C., then diluted with 4×10 L of $H_2O$. The resulting solution was extracted with 3×10 L of ethyl acetate, the organic phase was dried over anhydrous magnesium sulfate and concentrated, to provide the title compounds which were used directly without further purification.

Step B. N-(3,5-dibromobenzyl)-2,2-dimethoxyacetamide

To a 3-L 4-necked round-bottom flask purged and maintained with an inert atmosphere of nitrogen, was placed 1-(3,5-dibromophenyl)methanamine (771 g, 2.91 mmol, 1 equiv) and methyl 2,2-dimethoxyacetate (468.4 g, 3.49 mmol, 1.20 equiv). The resulting solution was stirred for 16 h at 130° C. in an oil bath. The reaction mixture was cooled to 25° C. with a water/ice bath. The residue was purified by flash column chromatography on silica gel (eluting with 50% EtOAc in Pet Ether) to give the title compound.

Step C. 5,7-dibromoisoquinolin-3-ol

To a 3-L 4-necked round-bottom flask purged and maintained with an inert atmosphere of nitrogen, was placed N-[(3,5-dibromophenyl)methyl]-2,2-dimethoxyacetamide (747 g, 2035.22 mmol, 1 equiv) and sulfuric acid (1.8 L, 1 equiv). The resulting solution was stirred for 16 h at 25° C. The reaction was then quenched by the addition of 10 L of water/ice. The solids were collected by filtration. The pH value of the solid was adjusted to 9 with $NaHCO_3$ (1 mol/L). The solids were collected by filtration to provide the title compound.

Step D. 3-(benzyloxy)-5,7-dibromoisoquinoline

To a 20-L 4-necked round-bottom flask purged and maintained with an inert atmosphere of nitrogen, was placed a solution of 5,7-dibromoisoquinolin-3-ol (552 g, 1822.06 mmol, 1 equiv) in THF (8.2 L). $Ag_2CO_3$ (301.5 g, 1.09 mmol, 0.60 equiv) was added and the solution was stirred at 65° C. for 30 minutes. To this solution was added (bromomethyl)benzene (342.8 g, 2004.27 mmol, 1.10 equiv). The resulting solution was stirred overnight at 60° C. The reaction mixture was cooled to 25° C. with a water/ice bath. The reaction was then quenched by the addition of 5 L of $NH_4Cl$. The resulting solution was extracted with 3×8 L of ethyl acetate. The organic phase was washed with 1×10 L of brine. The mixture was dried over anhydrous sodium sulfate and concentrated. The residue was purified by flash column chromatography on silica gel (eluting with 10% ethyl acetate/petroleum ether) to provide the title compound.

Step E. dimethyl 3-(benzyloxy)isoquinoline-5,7-dicarboxylate

To a 10-L pressure tank reactor, was placed a solution of 3-(benzyloxy)-5,7-dibromoisoquinoline (340 g, 864.97 mmol, 1 equiv) in MeOH (6.8 L), TEA (262.6 g, 2594.90 mmol, 3.0 equiv), dppf (47.8 g, 86.54 mmol, 0.10 equiv), and $Pd(AcO)_2$ (19.4 g, 86.50 mmol, 0.1 equiv). This was followed by the addition of CO (10 atm). The resulting solution was stirred overnight at 70° C. The reaction mixture was cooled to 25° C. with a water bath, diluted with 5 L of DCM, and concentrated. The resulting solid was washed with 5×3 L of MeOH to provide the title compound.

Step F. 3-(benzyloxy)-7-(methoxycarbonyl)isoquinoline-5-carboxylic acid and 3-(benzyloxy)-5-(methoxycarbonyl)isoquinoline-7-carboxylic acid To a 10-L 4-necked round-bottom flask purged and maintained with an inert atmosphere of nitrogen, was placed a solution of KOH (40.2 g, 716.51 mmol, 1.00 equiv) in $THF/H_2O$ (12.5 L/1.25 L). This was followed by the addition of a solution of 5,7-dimethyl 3-(benzyloxy)isoquinoline-5,7-dicarboxylate (252 g, 717.22 mmol, 1 equiv) in THF (2.5 L) dropwise with stirring. The resulting solution was stirred for 10 min at 0° C. The reaction was quenched by the addition of 15 L of DMSO. The reaction mixture was cooled to 0° C. with a water/ice bath and the pH value of the solution was adjusted to 2 with HCl (1 mol/L). The resulting solution was extracted with 3×7 L of dichloromethane dried over anhydrous sodium sulfate and concentrated. The residue was purified by flash column chromatography on silica gel (eluting with 5:1 dichloromethane:methanol) to provide the mixture of isomers. The title compounds were separated by chiral HPLC (IC, 3.0*100 mm, 10% to 50% MeOH (0.1% DEA)) to give faster eluting isomer intermediate 1 and slower eluting isomer intermediate 2. 1: $^1$H NMR (400 MHz, DMSO-d6, ppm): δ 13.58 (s, 1H), 9.44-9.35 (m, 1H), 9.02-8.92 (m, 1H), 8.81-8.73 (m, 1H), 8.25 (d, J=5.9 Hz, 1H), 7.54-7.47 (m, 2H), 7.45-7.29 (m, 3H), 5.52 (d, J=3.1 Hz, 2H), 3.95 (d, J=1.7 Hz, 3H). MS (ESI) m/z 338 (M+H) 2: $^1$H NMR (400 MHz, DMSO-d6, ppm): δ 13.49 (s, 1H), 9.44-9.36 (m, 1H), 8.98 (d, J=6.3 Hz, 1H), 8.81-8.74 (m, 1H), 8.13 (d, J=5.3 Hz, 1H), 7.55-7.48 (m, 2H), 7.45-7.30 (m, 3H), 5.53 (s, 2H), 3.96 (d, J=2.0 Hz, 3H), 3.35 (s, 2H). MS (ESI) m/z 338 (M+H).

Intermediate 3 methyl 3-(benzyloxy)-5-(piperidine-1-carbonyl)isoquinoline-7-carboxylate

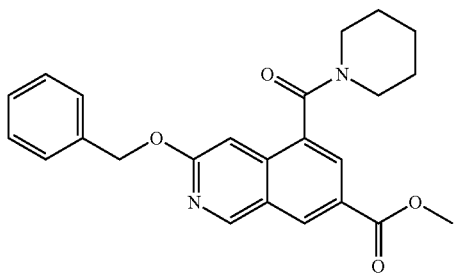 [SMILES: COC(=O)c1cc(C(=O)N2CCCCC2)c2cc(OCc3ccccc3)ncc2c1]

Step A: methyl 3-(benzyloxy)-5-(piperidine-1-carbonyl)isoquinoline-7-carboxylate To a solution of piperidine (379 mg, 4.45 mmol) and 3-(benzyloxy)-7-(methoxycarbonyl)isoquinoline-5-carboxylic acid (1000 mg, 2.96 mmol) in DMF (10 mL) was added HATU (1691 mg, 4.45 mmol) and DIPEA (2.071 mL, 11.86 mmol) at 25° C. in a round bottom flask. The reaction was stirred at 25° C. for 2 h. Water (20 mL) was added, and the mixture was extracted with EtOAc (30 mL×3), the combined organic layers were washed with brine (30 mL×3), dried over Na$_2$SO$_4$ and concentrated. The crude was purified by flash column chromatography on silica gel (0 to 20% Pet.ether/EA) to give the title compound. MS (ESI) m/z 405.2 (M+H).

EXAMPLES

Example 1

1-(3-(benzo[d]thiazol-2-ylmethoxy)-5-(piperidine-1-carbonyl)isoquinoline-7-carbonyl)-4-phenylpiperidine-4-carbonitrile

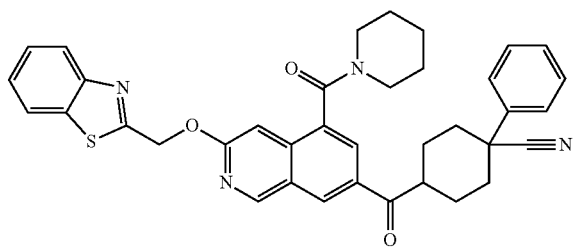 [SMILES: N#CC1(c2ccccc2)CCC(C(=O)c2cc(C(=O)N3CCCCC3)c3cc(OCc4nc5ccccc5s4)ncc3c2)CC1]

Synthetic Scheme:

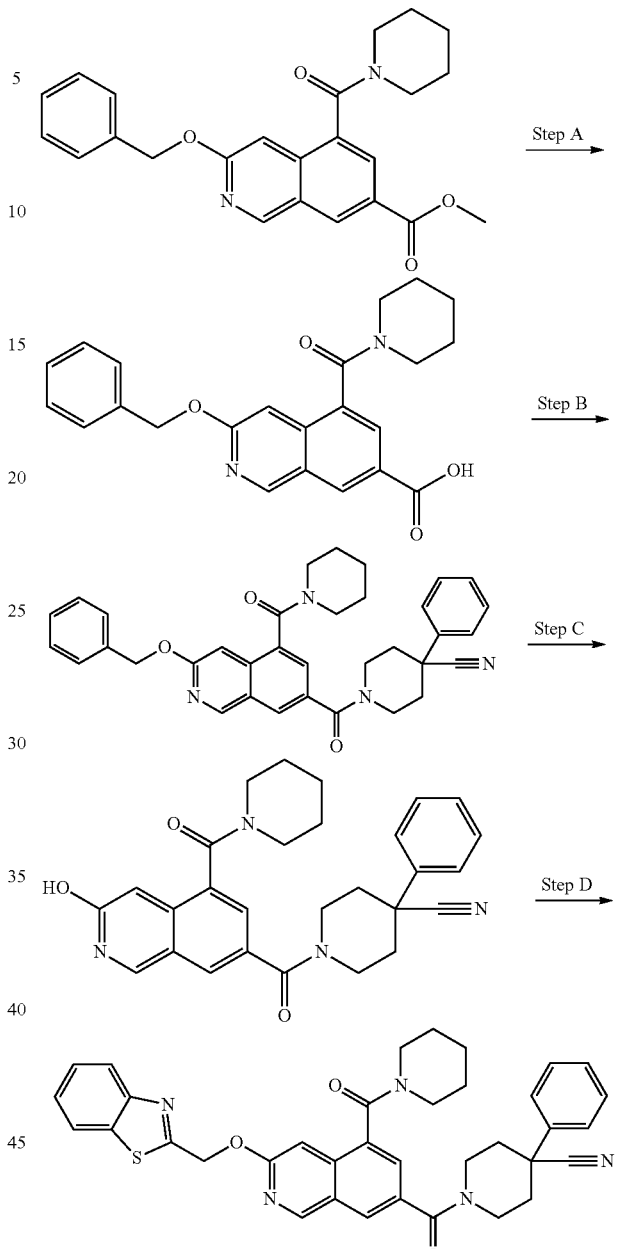

Step A: methyl 3-(benzyloxy)-5-(piperidine-1-carbonyl)isoquinoline-7-carboxylate To a solution of methyl 3-(benzyloxy)-5-(piperidine-1-carbonyl)isoquinoline-7-carboxylate (1.14 g, 2.82 mmol) in THF (20 mL) and water (5 mL) was added lithium hydroxide hydrate (0.237 g, 5.64 mmol) at 25° C. in a round bottom flask. The reaction was stirred at 25° C. for 16 h. Water (20 mL) was added, and the mixture was extracted with EA (30 mL×2). The aqueous layer was adjusted to pH 5 with 1 M HCl, extracted with EtOAc (30 mL×3), the combined organic layers were dried over Na$_2$SO$_4$ and concentrated to give the title compound which was used to the next step without further purification.
MS (ESI) m/z 391.1 (M+H).

Step B: 1-(3-(benzyloxy)-5-(piperidine-1-carbonyl) isoquinoline-7-carbonyl)-4-phenylpiperidine-4-carbonitrile To a solution of 3-(benzyloxy)-5-(piperidine-1-carbonyl) isoquinoline-7-carboxylic acid (1.1 g, 2.82 mmol) and 4-phenylpiperidine-4-carbonitrile hydrochloride (0.627 g, 2.82 mmol) in DMF (10 mL) was added HATU (1.607 g, 4.23 mmol) and DIPEA (1.968 mL, 11.27 mmol) at 25° C. in a round bottom flask. The reaction was stirred at 25° C. for 16 h. Water (20 mL) was added, and the mixture was extracted with EtOAc (30 mL×3), the combined organic layers were washed with brine (30 mL×3), dried over $Na_2SO_4$ and concentrated. The crude was purified by flash column chromatography on silica gel (eluting with 0-25% EtOAc in petroleum ether) to give the title compound. MS (ESI) m/z 559.3 (M+H).

Step C: 1-(3-hydroxy-5-(piperidine-1-carbonyl)isoquinoline-7-carbonyl)-4-phenylpiperidine-4-carbonitrile To a solution of 1-(3-(benzyloxy)-5-(piperidine-1-carbonyl)isoquinoline-7-carbonyl)-4-phenylpiperidine-4-carbonitrile (700 mg, 1.173 mmol) in DCM (5 mL) was added TFA (5 mL) at 25° C. in a round bottom flask. The reaction was stirred at 45° C. for 16 h. It was concentrated and EtOAc (30 mL) was added, the mixture was washed with $NaHCO_3$ (a.q., 30 mL) and brine (30 mL), dried over $Na_2SO_4$ and filtered. The filtrate was concentrated to give the title compound which was used to the next step without further purification. MS (ESI) m/z 469.2 (M+H).

Step D: 1-(3-(benzo[d]thiazol-2-ylmethoxy)-5-(piperidine-1-carbonyl)isoquinoline-7-carbonyl)-4-phenylpiperidine-4-carbonitrile To a solution of 2-(chloromethyl)benzo[d]thiazole (231 mg, 1.256 mmol) in DMF (15 mL) was added 1-(3-hydroxy-5-(piperidine-1-carbonyl)isoquinoline-7-carbonyl)-4-phenylpiperidine-4-carbonitrile (560 mg, 1.141 mmol), silver(I) oxide (529 mg, 2.283 mmol) and KI (18.95 mg, 0.114 mmol) at 25° C. in a round bottom flask. The reaction was stirred at 25° C. for 16 h, filtered, and purified by reverse phase HPLC (ACN/water with 0.05% TFA modifier) and lyophilized to give the title compound. MS (ESI) m/z 616.2 (M+H).

By using the procedures described above, and appropriate starting materials, the following compounds were synthesized and characterized by LC/MS.

| Ex. # | Structure | IUPAC Name | MS (M + 1) |
|---|---|---|---|
| 2 | 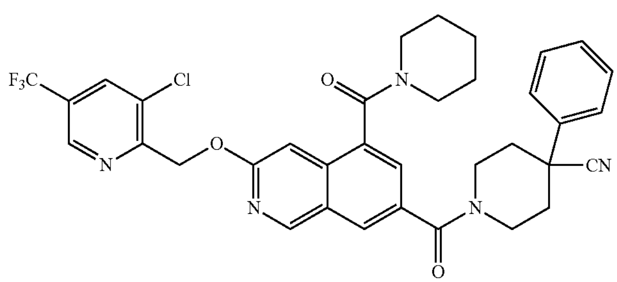 [SMILES: N#CC1(c2ccccc2)CCN(C(=O)c2cc(C(=O)N3CCCCC3)c3cc(OCc4ncc(C(F)(F)F)cc4Cl)ncc3c2)CC1] | 1-(3-((3-chloro-5-(trifluoromethyl)pyridin-2-yl)methoxy)-5-(piperidine-1-carbonyl)isoquinoline-7-carbonyl)-4-phenylpiperidine-4-carbonitrile | 662.2 |
| 3 | 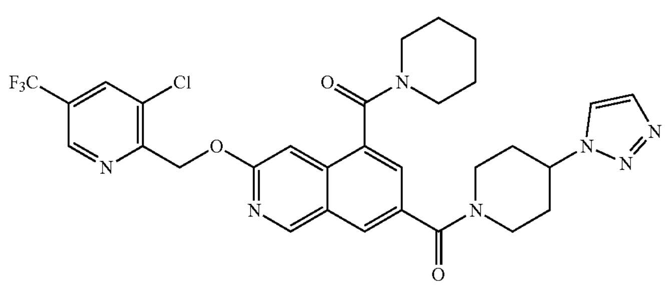 [SMILES: O=C(c1cc(C(=O)N2CCCCC2)c2cc(OCc3ncc(C(F)(F)F)cc3Cl)ncc2c1)N1CCC(n2ccnn2)CC1] | (4-(1H-1,2,3-triazol-1-yl)piperidin-1-yl)(3-((3-chloro-5-(trifluoromethyl)pyridin-2-yl)methoxy)-5-(piperidine-1-carbonyl)isoquinolin-7-yl)methanone | 628.2 |
| 4 | 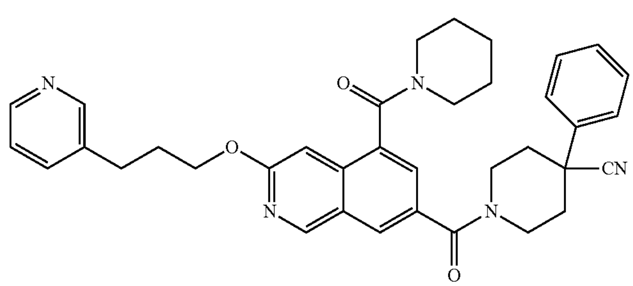 [SMILES: N#CC1(c2ccccc2)CCN(C(=O)c2cc(C(=O)N3CCCCC3)c3cc(OCCCc4cccnc4)ncc3c2)CC1] | 4-phenyl-1-(5-(piperidine-1-carbonyl)-3-(3-(pyridin-3-yl)propoxy)isoquinoline-7-carbonyl)piperidine-4-carbonitrile | 588.5 |

| Ex. # | Structure | IUPAC Name | MS (M + 1) |
|---|---|---|---|
| 5 | 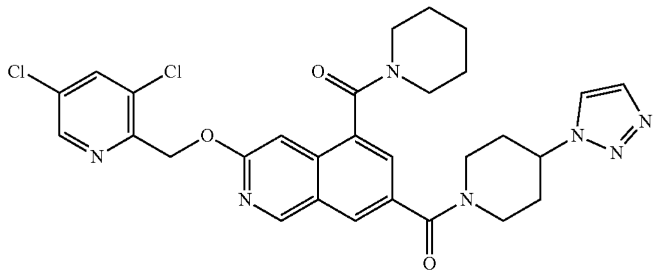 [SMILES: O=C(c1cc(C(=O)N2CCCCC2)c2cc(OCc3ncc(Cl)cc3Cl)ncc2c1)N1CCC(n2ccnn2)CC1] | (4-(1H-1,2,3-triazol-1-yl)piperidin-1-yl)(3-((3,5-dichloropyridin-2-yl)methoxy)-5-(piperidine-1-carbonyl)isoquinolin-7-yl)methanone | 594.2 |
| 6 | 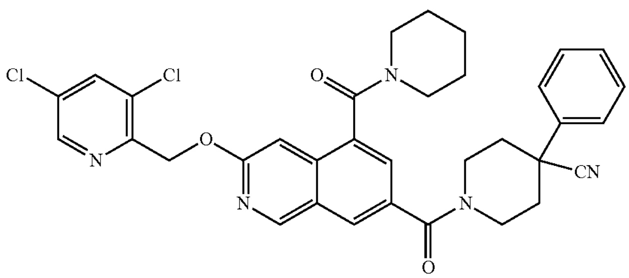 [SMILES: N#CC1(c2ccccc2)CCN(C(=O)c2cc(C(=O)N3CCCCC3)c3cc(OCc4ncc(Cl)cc4Cl)ncc3c2)CC1] | 1-(3-((3,5-dichloropyridin-2-yl)methoxy)-5-(piperidine-1-carbonyl)isoquinoline-7-carbonyl)-4-phenylpiperidine-4-carbonitrile | 628.3 |
| 7 | 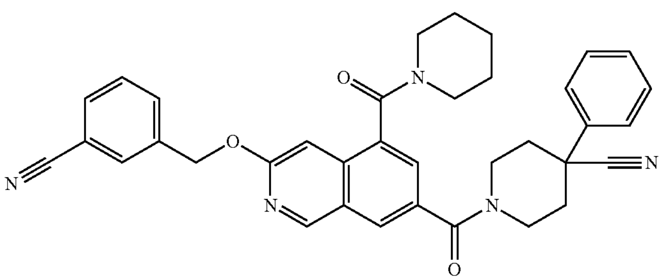 [SMILES: N#Cc1cccc(COc2cc3c(C(=O)N4CCCCC4)cc(C(=O)N4CCC(C#N)(c5ccccc5)CC4)cc3cn2)c1] | 1-(3-((3-cyanobenzyl)oxy)-5-(piperidine-1-carbonyl)isoquinoline-7-carbonyl)-4-phenylpiperidine-4-carbonitrile | 584.2 |

Example 8

(4-(1H-pyrazol-1-yl)piperidin-1-yl)(3-((3-chloro-5-(trifluoromethyl)pyridin-2-yl)methoxy)-5-(piperidine-1-carbonyl)isoquinolin-7-yl)methanone Synthetic Scheme:

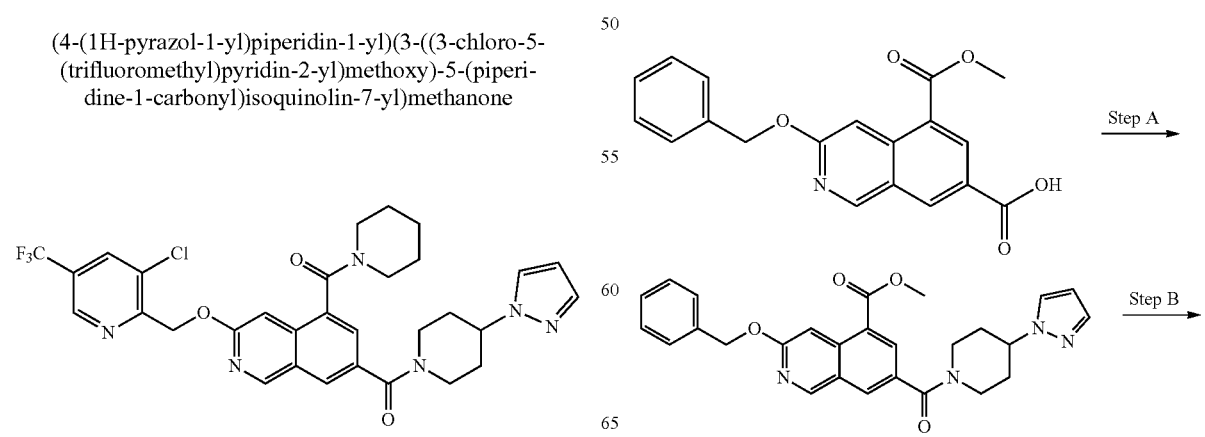

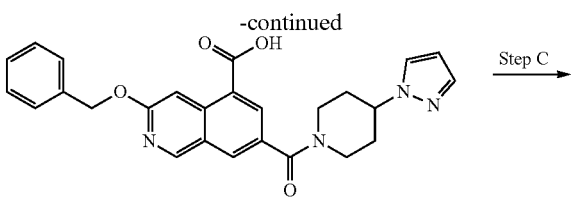

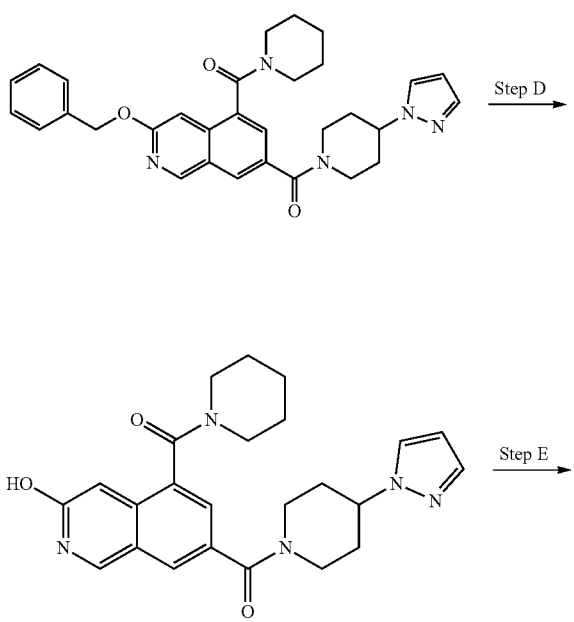

Step A: methyl 7-(4-(1H-pyrazol-1-yl)cyclohexane-1-carbonyl)-3-(benzyloxy)isoquinoline-5-carboxylate To a stirred mixture of 3-(benzyloxy)-5-(methoxycarbonyl)isoquinoline-7-carboxylic acid (1.5 g, 4.45 mmol), 4-(1H-pyrazol-1-yl)piperidine hydrochloride (0.97 g, 5.17 mmol), DIPEA (5 ml, 28.6 mmol) in DMF (20 ml) was added HATU (2.029 g, 5.34 mmol). The mixture was stirred at room temperature overnight. Hydrochloric acid (1M, 100 mL) was added and the mixture was extracted with ethyl acetate (3×80 mL). The combined organic fractions were washed with brine (saturated, 80 mL), dried over Na$_2$SO$_4$, filtered and concentrated. The residue was purified by flash column chromatography on silica gel (eluting with 0-100% EtOAc in hexane) to give the title compound. MS (ESI) m/z 471.3 (M+H).

Step B: 7-(4-(1H-pyrazol-1-yl)cyclohexane-1-carbonyl)-3-(benzyloxy)isoquinoline-5-carboxylic acid To a stirred mixture of methyl 7-(4-(1H-pyrazol-1-yl)piperidine-1-carbonyl)-3-(benzyloxy)isoquinoline-5-carboxylate (2 g, 4.25 mmol) in THF (10 ml) and water (10.00 ml) was added LiOH (0.305 g, 12.75 mmol) and the mixture was stirred at room temperature overnight. Hydrochloric acid (1M, 100 mL) was added and the mixture was extracted with ethyl acetate (3×80 mL). The combined organic fractions were concentrated and dried to provide the title compound. MS (ESI) m/z 457.3 (M+H).

Step C: (4-(1H-pyrazol-1-yl)piperidin-1-yl)(3-(benzyloxy)-5-(piperidine-1-carbonyl)isoquinolin-7-yl)methanone To a stirred mixture of 7-(4-(1H-pyrazol-1-yl)piperidine-1-carbonyl)-3-(benzyloxy)isoquinoline-5-carboxylic acid (961.8 mg, 2.107 mmol), piperidine (0.312 ml, 3.16 mmol), and DIPEA (3, 17.18 mmol) in DMF (20 ml) was added HATU (1602 mg, 4.21 mmol) and the mixture was stirred at room temperature for 3 h. Hydrochloric acid (1M, 100 mL) was added and the mixture was extracted with ethyl acetate (3×80 mL). The combined organic fractions were washed with brine (80 mL), dried over Na$_2$SO$_4$, filtered and concentrated. The residue was purified by flash column chromatography on silica gel (eluting with 0-100% EtOAc in hexane) to give the title compound. MS (ESI) m/z 524.4 (M+H).

Step D: (4-(1H-pyrazol-1-yl)piperidin-1-yl)(3-hydroxy-5-(piperidine-1-carbonyl)isoquinolin-7-yl)methanone To a stirred mixture of (4-(1H-pyrazol-1-yl)piperidin-1-yl)(3-(benzyloxy)-5-(piperidine-1-carbonyl)isoquinolin-7-yl)methanone (577 mg, 1.102 mmol) was added HCl (2 mL, 6 N, 12.00 mmol) and the mixture was stirred at 100° C. for 15 min. The reaction was concentrated to provide the title compound which was used to the next step without further purification. MS (ESI) m/z 434.3 (M+H).

Step E: (4-(1H-pyrazol-1-yl)piperidin-1-yl)(3-((3-chloro-5-(trifluoromethyl)pyridin-2-yl)methoxy)-5-(piperidine-1-carbonyl)isoquinolin-7-yl)methanone To a stirred mixture of (4-(1H-pyrazol-1-yl)piperidin-1-yl)(3-hydroxy-5-(piperidine carbonyl)isoquinolin-7-yl)methanone (35.4 mg, 0.082 mmol) and silver carbonate (137 mg, 0.497 mmol) in toluene (2 ml), was added 3-chloro-2-(chloromethyl)-5-(trifluoromethyl)pyridine (37.6 mg, 0.163 mmol) in toluene (1 mL) and the mixture was stirred at 100° C. overnight. The reaction mixture was concentrated, dissolved in MeOH (2 mL), filtered, and purified by reverse phase HPLC (ACN/water with 0.05% TFA modifier) and lyophilized to give the title compound. MS (ESI) m/z 627.3 (M+H).

By using the procedures described above, and appropriate starting materials, the following compounds were synthesized and characterized by LC/MS.

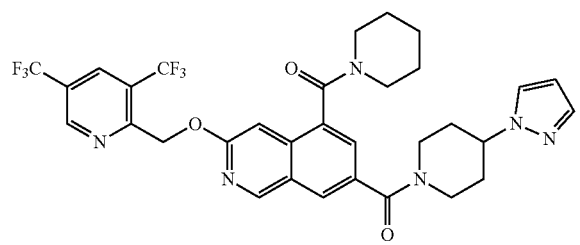

| Ex. # | Structure | IUPAC Name | MS (M + 1) |
|---|---|---|---|
| 9 | 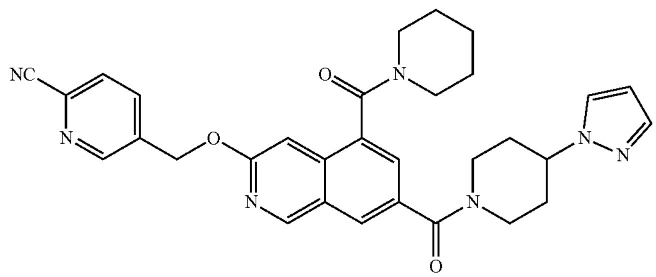 [SMILES: N#Cc1ccc(COc2cc3c(C(=O)N4CCCCC4)cc(C(=O)N4CCC(n5cccn5)CC4)cc3cn2)cn1] | 5-(((7-(4-(1H-pyrazol-1-yl)piperidine-1-carbonyl)-5-(piperidine-1-carbonyl)isoquinolin-3-yl)oxy)methyl)picolinonitrile | 550.4 |
| 10 | 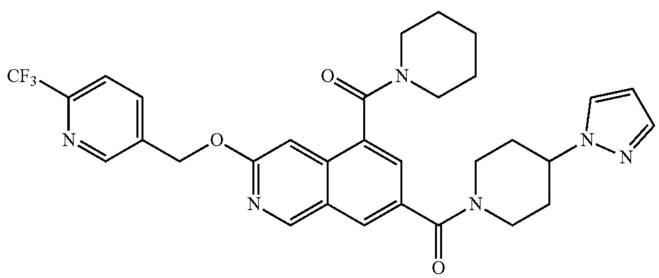 [SMILES: O=C(c1cc(C(=O)N2CCCCC2)c2cc(OCc3ccc(C(F)(F)F)nc3)ncc2c1)N1CCC(n2cccn2)CC1] | (4-(1H-pyrazol-1-yl)piperidin-1-yl)(5-(piperidine-1-carbonyl)-3-((6-(trifluoromethyl)pyridin-3-yl)methoxy)isoquinolin-7-yl)methanone | 593.4 |
| 11 | 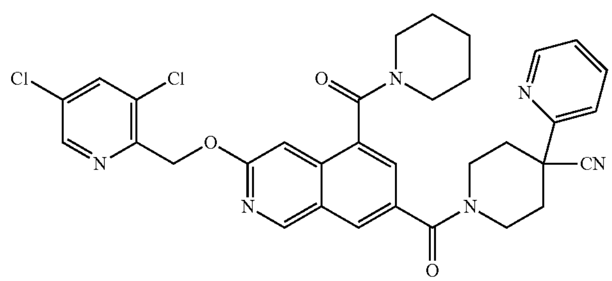 [SMILES: N#CC1(c2ccccn2)CCN(C(=O)c2cc(C(=O)N3CCCCC3)c3cc(OCc4ncc(Cl)cc4Cl)ncc3c2)CC1] | 1-(3-((3,5-dichloropyridin-2-yl)methoxy)-5-(piperidine-1-carbonyl)isoquinoline-7-carbonyl)-4-(pyridin-2-yl)piperidine-4-carbonitrile | 629.3 |
| 12 | 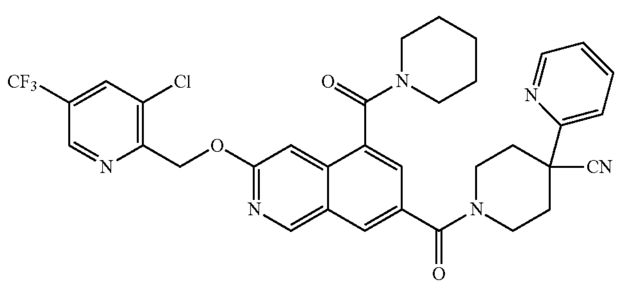 | 1-(3-((3-chloro-5-(trifluoromethyl)pyridin-2-yl)methoxy)-5-(piperidine-1-carbonyl)isoquinoline-7-carbonyl)-4-(pyridin-2-yl)piperidine-4-carbonitrile | 663.3 |
| 13 | 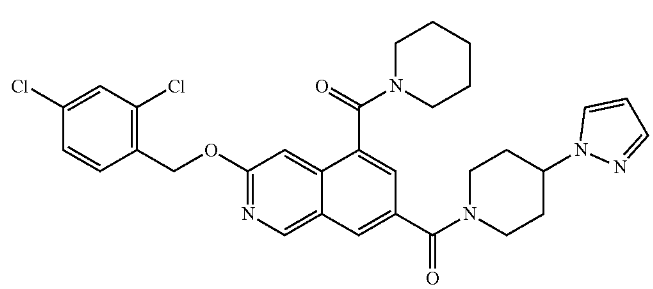 [SMILES: O=C(c1cc(C(=O)N2CCCCC2)c2cc(OCc3ccc(Cl)cc3Cl)ncc2c1)N1CCC(n2cccn2)CC1] | (4-(1H-pyrazol-1-yl)piperidin-1-yl)(3-((2,4-dichlorobenzyl)oxy)-5-(piperidine-1-carbonyl)isoquinolin-7-yl)methanone | 592.3 |

| Ex. # | Structure | IUPAC Name | MS (M + 1) |
|---|---|---|---|
| 14 | 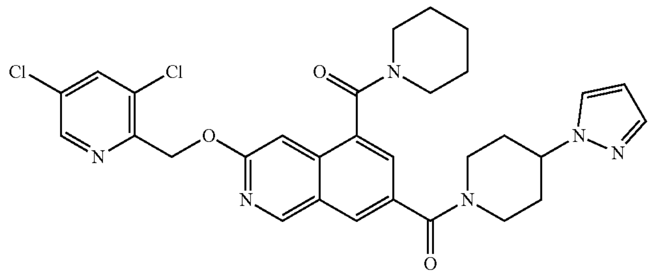 [SMILES: O=C(c1cc(C(=O)N2CCCCC2)c2cc(OCc3ncc(Cl)cc3Cl)ncc2c1)N1CCC(n2cccn2)CC1] | (4-(1H-pyrazol-1-yl)piperidin-1-yl)(3-((3,5-dichloropyridin-2-yl)methoxy)-5-(piperidine-1-carbonyl)isoquinolin-7-yl)methanone | 593.3 |
| 15 | 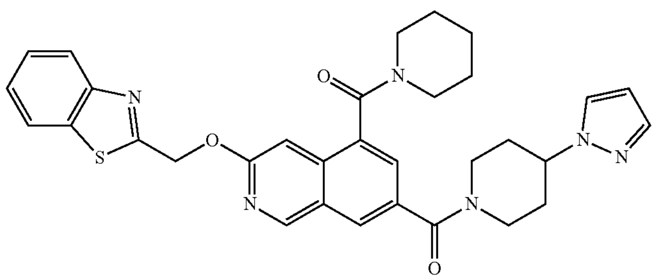 [SMILES: O=C(c1cc(C(=O)N2CCCCC2)c2cc(OCc3nc4ccccc4s3)ncc2c1)N1CCC(n2cccn2)CC1] | (4-(1H-pyrazol-1-yl)piperidin-1-yl)(3-(benzo[d]thiazol-2-ylmethoxy)-5-(piperidine-1-carbonyl)isoquinolin-7-yl)methanone | 581.4 |

Example 16

(3-((3-chloro-5-(trifluoromethyl)pyridin-2-yl)methoxy)-5-(piperidine-1-carbonyl)isoquinolin yl)(4-(4-methyl-1H-pyrazol-1-yl)piperidin-1-yl)methanone Synthetic Scheme:

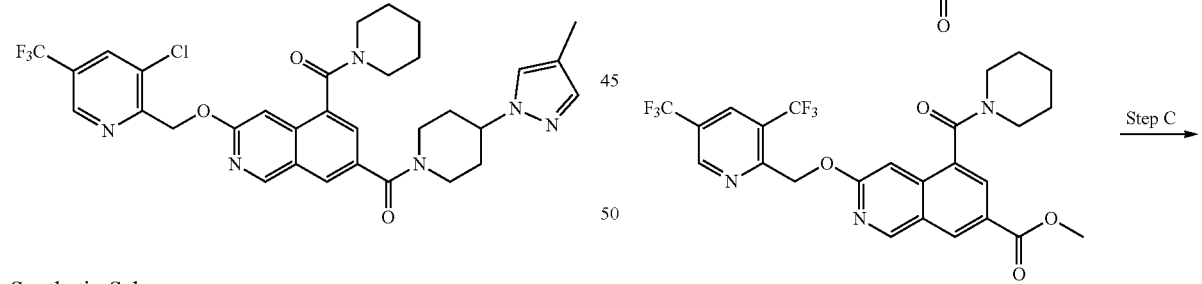

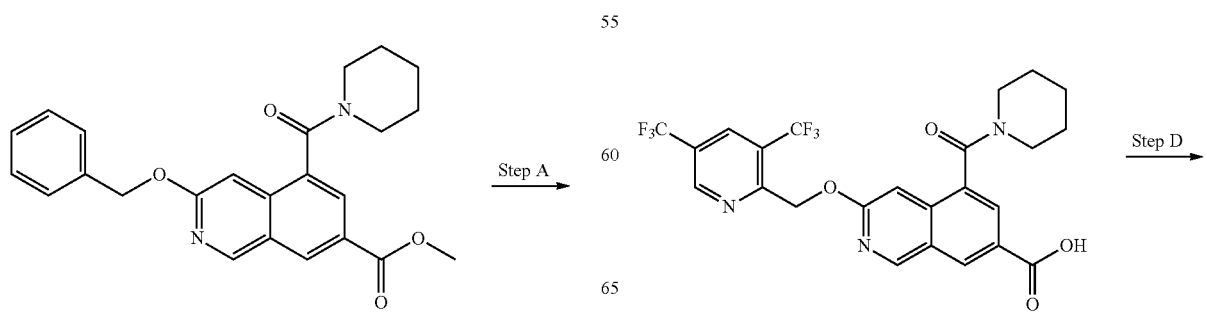

-continued

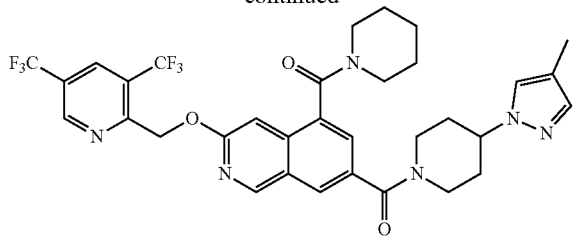

Step A: 3-hydroxy-5-(piperidine-1-carbonyl)isoquinoline-7-carboxylate

To a solution of (methyl 3-(benzyloxy)-5-(piperidine-1-carbonyl)isoquinoline-7-carboxylate (50 mg, 0.124 mmol) in MeOH (5 ml) and ethyl acetate (5.00 ml) was added Pd/C (7.89 mg, 7.42 μmop. The reaction was stirred under $H_2$ balloon at room temperature for 30 mins. The mixture was filtered and the filtrate was concentrated to give the title compound, which was used in the next step without purification. MS (ESI) m/z 315.0 (M+H).

Step B: methyl 3-((3-chloro-5-(trifluoromethyl)pyridin-2-yl)methoxy)-5-(piperidine-1-carbonyl)isoquinoline-7-carboxylate To a solution of methyl 3-(benzyloxy)-5-(piperidine-1-carbonyl)isoquinoline-7-carboxylate (1.14 g, 2.82 mmol) in $CHCl_3$ (1 ml) was added silver carbonate (102 mg, 0.369 mmol) and methyl 3-hydroxy-5-(piperidine-1-carbonyl)isoquinoline-7-carboxylate (43 mg, 0.123 mmol). The reaction mixture was stirred at rt for 2 days, then filtered through celite and concentrated. The residue was purified by flash column chromatography on silica gel (0-100% Hexane: (3:1 EtOAC:MeOH)) to give the title compound. MS (ESI) m/z 508.0 (M+H).

Step C: 3-((3-chloro-5-(trifluoromethyl)pyridin-2-yl)methoxy)-5-(piperidine-1-carbonyl)isoquinoline-7-carboxylic acid To a solution of methyl 3-((3-chloro-5-(trifluoromethyl) pyridin-2-yl)methoxy)-5-(piperidine carbonyl)isoquinoline-7-carboxylate (46 mg, 0.091 mmol) in a mixed solvent of THF (1 ml) and water (0.50 ml) was added lithium hydroxide hydrate (10.85 mg, 0.453 mmol). The reaction was stirred at 40° C. overnight, then diluted with water (1 mL) and adjusted to pH 2 with 2 M HCl. The mixture was filtered, and the filter cake was dried under vacuum to give the title compound, which was used to next step without purification. MS (ESI) m/z 494.0 (M+H).

Step D: (3-((3-chloro-5-(trifluoromethyl)pyridin-2-yl)methoxy)-5-(piperidine-1-carbonyl)isoquinolin-7-yl)(4-(4-methyl-1H-pyrazol-1-yl)piperidin-1-yl)methanone To a solution of 3-((3-chloro-5-(trifluoromethyl)pyridin-2-yl)methoxy)-5-(piperidine-1-carbonyl)isoquinoline-7-carboxylic acid hydrochloride (16 mg, 0.030 mmol) and 4-(4-methyl-1H-pyrazol-1-yl)piperidine 2,2,2-trifluoroacetate (10.11 mg, 0.036 mmol) in DMF (10 mL) was added HATU (13.77 mg, 0.036 mmol) and DIEA (0.021 ml, 0.121 mmol). The reaction was stirred at rt for 16 h. The mixture was purified by reverse phase HPLC (ACN/water with 0.05% TFA modifier) and lyophilized to give the title compound. MS (ESI) m/z 641.3 (M+H).

Inhibition of FXIIa Mediated Activation of FXI

Activation of Human Factor XI to XIa by Human Factor α-XIIa

The assay was performed in 50 mM HEPES, 150 mM NaCl, 5 mM $CaCl_2$, 0.1% PEG-8000, pH 7.4 buffer in black, flat-bottom, polystyrene microplates (Corning, Cat #3573). Serial dilutions (10-point, 3.333-fold) of the test compounds delivered as 10 mM DMSO stocks were prepared in the Labcyte Echo-qualified PP 384 well microplates (Labcyte, Cat #P-05525). Human coagulation factor (F)XI (Haematologic Technologies Inc., Cat #HCXI-150, concentration 46 nM, 19.5 uL) was pre-incubated with 0.5 uL of the test compounds for 30 min at 22° C. The activation was initiated by addition of 10 uL of human coagulation factor (F)XIIa (Enzyme Research Laboratories, Cat #HFXIIa, concentration 30 nM) and the reaction proceeded for 60 min at 22° C., after which it was quenched by addition of a selective inhibitor of FXIIa (Compound 54 in WO2018093695) concentration 600 uM in DMSO, 1 uL. 10 min after the quench, 29 uL of z-GPR-AFC substrate (Sigma, Cat #C0980-10MG, concentration 200 uM) was added into each well and the detection reaction proceeded for 60 min at 22° C. Fluorescence at 405/510 nm was measured in end-point mode using an Envision plate-reader (Perkin Elmer). IDBS Activity Base XE (ABase) analysis using 4 parameter logistic fit was performed to determine Minimum, Maximum, EC50, and Slope Factor for each compound.

| Example # | Inhibition of FXIIa meditated activation of FXI (nM) |
|---|---|
| 1 | 37.9 |
| 2 | 26.8 |
| 3 | 32.7 |
| 4 | 8.5 |
| 5 | 41.0 |
| 6 | 19.4 |
| 7 | 23.6 |
| 8 | 13.4 |
| 9 | 45.7 |
| 10 | 33.2 |
| 11 | 4.3 |
| 12 | 24.3 |
| 13 | 49.5 |
| 14 | 8.8 |
| 15 | 19.9 |
| 16 | 3.8 |

What is claimed is:

1. A compound of the formula:

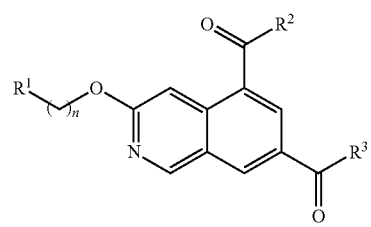

wherein
- R¹ is phenyl or heteroaryl, which may be monocyclic or bicyclic, wherein said phenyl and heteroaryl groups are optionally substituted with one to three substituents independently selected from the group consisting of halo, oxo, cyano, R⁴ and OR⁴;
- R² is piperidinyl or NR⁴R⁵, wherein said piperidinyl group is optionally substituted with one to three halo;
- R³ is heterocyclyl, which is optionally substituted with one to three substituents independently selected from the group consisting of halo, cyano, R⁴, OR⁴ and R⁶;
- R⁴ is hydrogen or C₁₋₆ alkyl, which is optionally substituted with one to three halo;
- R⁵ is hydrogen or C₁₋₆ alkyl, which is optionally substituted with one to three halo;
- R⁶ is phenyl, C₃₋₆ cycloalkyl, heterocyclyl or heteroaryl, wherein said heteroaryl is optionally substituted with one to three substituents independently selected from the group consisting of C₁₋₆ alkyl and halo;
- n is an integer from one to three;
- or a pharmaceutically acceptable salt thereof.

2. The compound of claim 1 wherein R¹ is selected from benzothiazolyl, phenyl or pyridinyl wherein said groups are optionally substituted with one or two substituents independently selected from the group consisting of chloro, cyano and CF₃; or a pharmaceutically acceptable salt thereof.

3. The compound of claim 1 wherein R² is piperidinyl, or a pharmaceutically acceptable salt thereof.

4. The compound of claim 1 wherein R³ is piperidinyl, which is optionally substituted with one or two substituents independently selected from the group consisting of cyano, pyrazolyl, methylpyrazolyl, phenyl and triazolyl; or a pharmaceutically acceptable salt thereof.

5. The compound of claim 1 wherein R³ is piperidinyl, which is optionally substituted with cyano and phenyl; or a pharmaceutically acceptable salt thereof.

6. The compound of claim 1 wherein n is one; or a pharmaceutically acceptable salt thereof.

7. The compound selected from

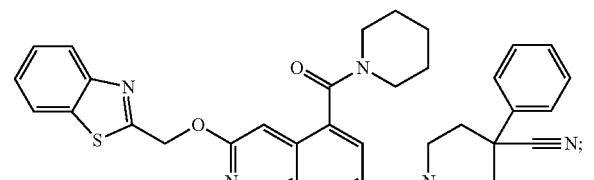

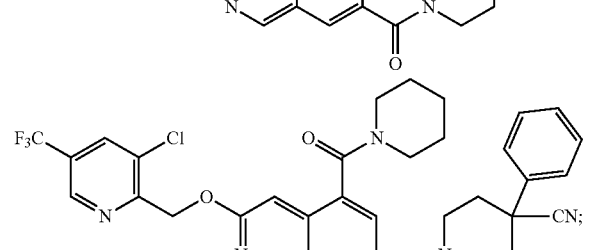

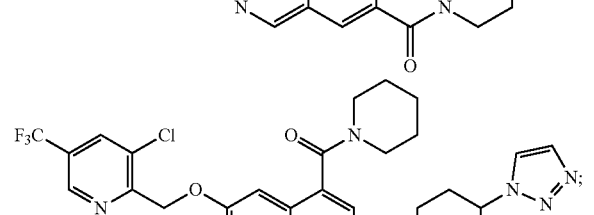

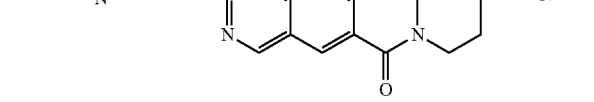

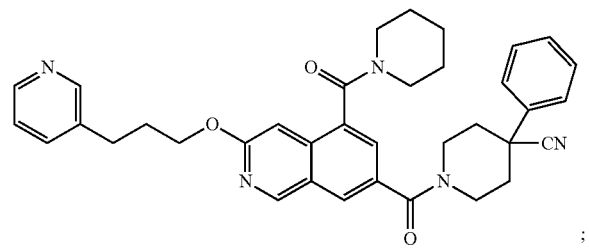

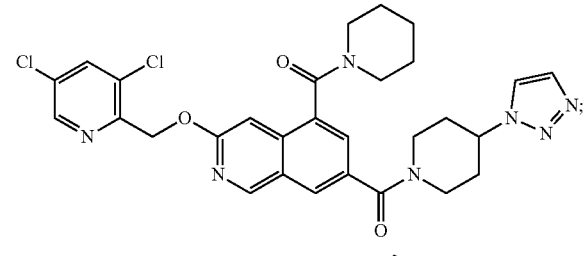

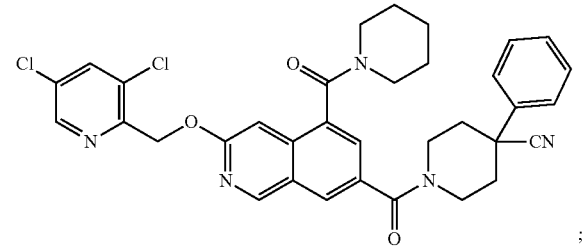

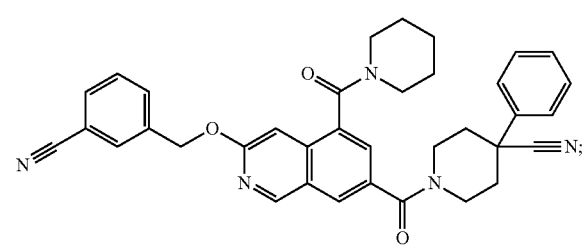

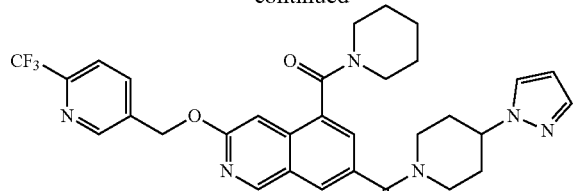

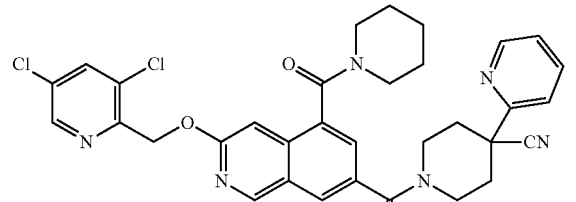

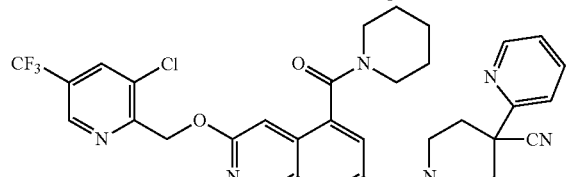

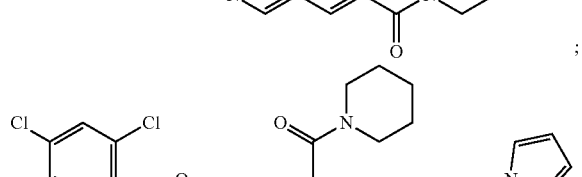

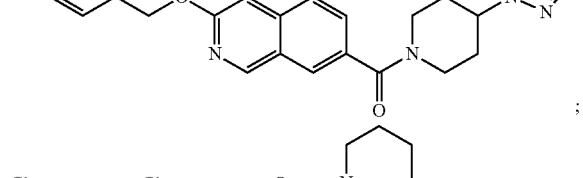

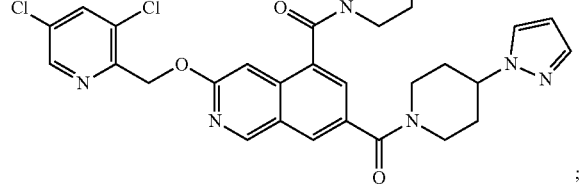

or a pharmaceutically acceptable salt thereof.

8. A pharmaceutical composition comprising a compound of claim 1 or a pharmaceutically acceptable salt thereof and a pharmaceutically acceptable carrier.

9. A method for inhibiting thrombus formation in blood or treating thrombus formation in blood comprising administering a composition of claim 8 to a mammal in need of thereof.

10. A method for preventing thrombus formation in blood comprising administering a composition of claim 8 to a mammal in need thereof.

11. A method of treating venous thromboembolism or pulmonary embolism in a mammal comprising administering a composition of claim 8 to a mammal in need thereof.

12. A method of treating deep vein thrombosis in a mammal comprising administering a composition of claim 8 to a mammal in need thereof.

13. A method of treating thromboembolic stroke in a mammal comprising administering a composition of claim 1 to a mammal in need thereof.

\* \* \* \* \*